(12) United States Patent
Flanagan et al.

(10) Patent No.: US 8,210,681 B2
(45) Date of Patent: Jul. 3, 2012

(54) METHOD AND DEVICE FOR ASSESSING THE FIELD OF VISION

(75) Inventors: John Flanagan, Kitchener (CA); James Cassidy, Waterloo (CA)

(73) Assignee: Heidelberg Engineering GmbH, Heidelberg (DE)

( * ) Notice: Subject to any disclaimer, the term of this patent is extended or adjusted under 35 U.S.C. 154(b) by 46 days.

(21) Appl. No.: 12/669,669

(22) PCT Filed: Jul. 17, 2008

(86) PCT No.: PCT/EP2008/005858
§ 371 (c)(1),
(2), (4) Date: Jul. 20, 2010

(87) PCT Pub. No.: WO2009/010291
PCT Pub. Date: Jan. 22, 2009

(65) Prior Publication Data
US 2010/0290006 A1    Nov. 18, 2010

(30) Foreign Application Priority Data
Jul. 17, 2007  (DE) .......................... 10 2007 033 614

(51) Int. Cl.
*A61B 3/14*  (2006.01)

(52) U.S. Cl. .......................... 351/209; 351/246; 351/200

(58) Field of Classification Search .................. 351/200, 351/209, 246
See application file for complete search history.

(56) References Cited

U.S. PATENT DOCUMENTS

| | | | |
|---|---|---|---|
| 4,063,807 A * | 12/1977 | Gelius et al. .................. | 351/226 |
| 5,061,060 A * | 10/1991 | Aulhorn et al. ............... | 351/224 |
| 5,270,750 A | 12/1993 | Aulhorn et al. | |
| 6,592,222 B2 * | 7/2003 | Massengill et al. ........... | 351/237 |
| 2002/0047987 A1 | 4/2002 | Massengill et al. | |

FOREIGN PATENT DOCUMENTS

| | | |
|---|---|---|
| DE | 196 49 858 | 6/1998 |
| DE | 102 33 960 | 2/2004 |
| EP | 0 962 188 | 12/1999 |
| EP | 1 397 991 | 3/2004 |
| EP | 1 442 695 | 8/2004 |
| WO | WO-01/43637 | 6/2001 |
| WO | WO-01/60241 | 8/2001 |

OTHER PUBLICATIONS

E. Sutter et. al.; "The field topography of ERG components in Man-I. The photopic luminance response"; Vision Research, Pergamon Press, Oxford, GB, vol. 32, No. 3, Mar. 1, 1992, pp. 433-446, XP022178094.

(Continued)

*Primary Examiner* — James Greece
(74) *Attorney, Agent, or Firm* — Jordan and Hamburg LLP

(57) ABSTRACT

The invention relates to a method for assessing the field of vision, wherein FDF stimuli are produced and detected by a person using the at least one eye to be examined. The invention is based on the object of providing a novel method and a device in order to efficiently assess the field of vision of a person and/or in order to recognize early signs of disease processes, which can lead to limitations in the field of vision. For this purpose, the invention provides that the production of the FDF stimuli is carried out by utilizing a computer-controlled system for the efficient determination of the vision and that the respective FDF stimulus is generated by utilizing an imaging device.

12 Claims, 3 Drawing Sheets

OTHER PUBLICATIONS

V. S. Ramachandran et al., "Phantom contours: A new class of visual patterns that selectively activates the magnocellular pathway in man"; Bulletin of Psychonomic Society, 1991, 29 (5), pp. 391-394.

P.T. Quaid et al., "Defining the limits of flicker defined form: effect of stimulus size, eccentricity and Number of random dots"; Vision Research 45, (2005), pp. 1075-1084.

* cited by examiner

METHOD AND DEVICE FOR ASSESSING THE FIELD OF VISION

BACKGROUND OF THE INVENTION

The invention relates to a method for evaluating the field of vision. The invention furthermore relates to an apparatus for performing the method.

Known from WO 01/60 241 A1 are for instance a method and an apparatus for examining an eye, an image acquisition unit embodied as a camera and an illumination unit being used in conjunction with a computer-supported image evaluation. The illumination unit includes a light source, such as for instance a laser, and a deflection unit or scanning unit, by means of which the light beam from the light source is deflected two-dimensionally in a plane and at least some of the eye, for instance the surface of the retina, is scanned. The reflected light beam is detected by means of the image acquisition unit and a computer evaluates the acquired images, especially using optical coherence tomography (OCT), for representing planar images by means of an image generating device. The apparatus or the opthalmoscope includes closed control circuits with a motor control for an illumination lens for the purpose of automatic focus adjustment of an imaging lens. Moreover, the brightness of the illumination unit is adjustable for the purpose of attaining good contrast and good illumination of the eye to be imaged or of an area of the eye to be imaged.

Furthermore known is a method for examining field of vision, which method is based on representing a stimulus and is described in the publication "Ramachandran V. S., Rogers Ramachandran D.: Phantom Contours: A New Class of Visual Patterns that Selectively Activates the Magnocellular Pathway in Man. Bulletin of the Psychonomic Society, 2, 391 (1992)". The method or depiction of the stimulus is known as "flicker defined form" and shall be referred to hereinafter as FDF.

The underlying object of the invention is to propose a novel method and an apparatus in order to efficiently evaluate the field of vision of a person and/or in order to detect in particular early signs of disease processes that can lead to limitations in the field of vision. The method and the apparatus should furthermore be embodied and/or optimized such that results for the field of vision examination are combined with results of a structural evaluation of the optic disc in an eye in order to increase diagnostic capability, especially for diseases such as glaucoma that lead to both functional changes in the field of vision and to structural changes in the optic disc. The underlying object of the invention is furthermore to refine the method and the apparatus such that the examination and/or evaluation of the field of vision can be performed in a simple manner and/or such that confidence in decision-making is optimized. Moreover, rapid and reliable testing and/or evaluation should be possible, subjective evaluations being avoided.

SUMMARY OF THE INVENTION

The inventive method and the apparatus enable complete and especially automatic evaluation using a computer-controlled system for representing FDF stimuli for efficient determination of visual function. The invention discloses a novel method and a novel apparatus and makes possible efficient evaluation in particular of the field of vision of a person in order to detect in particular early signs of disease processes that can lead to limitations in the field of vision. In accordance with the invention, results of the field of vision examination are combined with results of the structural evaluation especially of the optic disc in order to increase diagnostic capability, especially for diseases such as glaucoma that lead to both functional changes in the field of vision and to structural changes in the optic disc.

In accordance with the invention, a method for eye examination or a device or system embodied therefor, such as perimeter, confocal laser scanning system, OCT interferometer, or scanning laser opthalmoscope is combined with the FDF method or an FDF device. Simultaneous acquisition and representation and/or examinations and/or evaluations of functional and/or structural changes in the eye are made possible in a surprisingly simple manner by using the inventive combination and/or integration creating a single method and/or a single apparatus.

The FDF stimulus comprises and/or uses and/or occurs with an image generating unit, such as a monitor or cathode ray tube (CRT), flat screen, projection device, or the like, and specifically especially with the same common image generating unit. The application of the FDF examination using the inventive method and/or by means of the inventive apparatus reliably enable the use of FDF perimetry in order to perform examinations of the eye, especially for glaucoma, optic nerve and/or retinal disease and abnormalities, eye disease due to diabetes, and neurological disease and abnormalities. Furthermore, in accordance with the invention, patients with low vision, patients with special needs, and some patients with learning disabilities can be examined according to the inventive method and/or with the inventive apparatus.

In one special embodiment of the invention, a method and/or an apparatus for determining an artifact and/or the beginning of a stimulus for correcting or detecting an artifact and/or for stimulus beginning artifact correction are used. An FDF stimulus comprises and/or uses an image generating unit (CRT display, LCD display, projection device, or the like) on which numerous circular objects or points are displayed against a solid background. The recordable surface of the image generating unit is filled with these points in a preferred manner and/or is at least nearly essentially filled with these points and/or is completely filled with these points. The aforesaid points are classified in two categories, specifically background points and target points. The background points preferably cover the majority of the visible display. One circular area of the display unit and/or the image generating unit is intended for representing the stimulus and the points that are disposed and/or located inside the stimulus area are classified and/or categorized as target points.

During the representation of the FDF stimulus, which hereinafter shall be referred to only as FDF stimulus, the points move between two brightnesses or intensity values at a fixed frequency. The first level is a fixed luminosity value above the background luminosity. And the second brightness is the same luminosity value below the background luminosity. However, it is important to note that during the stimulus representation the background points and the target points are in phase opposition. For instance, when the target points are brighter than the background luminosity, the background points are darker than the background luminosity and vice versa.

Another special embodiment of the inventive method and/or apparatus makes it possible to evaluate the fatigue of the person being examined by using a real-time focusing monitor. While the FDF examination is being performed, targets are represented at different locations relative to the optical axis of the instrument. In order to support the fixed gaze or focusing on this point, a small black point is provided (focusing target). In addition, a means for verifying the correctness of the focusing during the period in which the target is represented is provided so that the coordinates of the different target eccentricities are correct.

This verification is provided by an image acquisition unit, such as a small CCD camera, that observes the examined eye of the person either directly or via a beam splitter that is arranged in the optical axis between the person and the display. The images are processed by the computer, which uses algorithms to determine the point of the fixed gaze of the person and/or to detect the correct focusing. This is done by identifying characteristic structures in the eye, for instance the pupil, and by continuously tracking the position of this structure during the FDF examination.

This tracking is performed by analyzing the image of the image generating unit or CCD camera with the computer. When the computer determines that the person was not focused during the target representation, or when this is determined by means of the computer, the results of such an acquisition and/or representation are discarded.

In addition, information regarding the degree of fatigue of the person can be derived from the focus loss rate. This information can be used to evaluate the quality of the examination results, or to indicate that the person needs a break from the examination.

In another special embodiment of the method and/or apparatus, it is possible to evaluate a patient's reliability by using continuous reaction time monitoring. The inventively developed and/or proposed method and/or the apparatus used for performing said method makes it possible to continuously monitor a patient's reaction time to the representation of the FDF stimulus.

The reaction time is measured as the time, especially in milliseconds, between a target representation being initiated and the patient depressing the response button. This is monitored for every target representation during an examination, and a concurrent mean is calculated, together with confidence limits. Each response that falls outside the 95th percentile is evaluated either as a false positive (<) or an unreliable response (>).

One special use of this data is comprised in establishing individual reaction time characteristics and patient-related confidence limits in order to determine the probability of whether a response is a false positive response. This information can then itself be used to establish reliability parameters.

In another embodiment according to the method and/or with the apparatus there is a boundary field examination. Adding light sources, especially LEDs, that are arranged physically and/or optically especially in the horizontal boundary field results in the unique and/or special ability to measure and/or evaluate especially fitness for driving or possibly special neurological areas.

In one special refinement and/or embodiment of the method and/or apparatus, these are embodied for controlling an increased brightness resolution. Standard graphics card technology provides $2^8$, or 256 levels of brightness, for each of the red, green, and blue color channels. A technique was developed in which the one monochrome screen (CRT, LCD, or a projection device) uses two of the color channels in order to provide brightness levels with up to $2^{16}$, or 65536, brightness levels.

The method and/or the apparatus preferably use especially the green and red channels of an RGB signal with 8 bits brightness control per channel such that the resultant control is a monochrome channel with 16 bits intensity or brightness regulation. The green channel is used as the 8 bits with the greatest significance. Therefore one level of the green channel is responsible for a brightness increment of $1/256$ of the maximum. The red channel is used as the 8 bits with the least significance. Therefore one level of the red channel is responsible for a brightness increment of $1/65536$ of the maximum. The resulting two signals are added with the resulting intensity or brightness control function:

$$\text{Brightness} = \text{maximum brightness} \cdot \left[\frac{G}{256} + \frac{R}{65536}\right]$$

where G is the green signal level, the values of which range from 0 to 255, and R is the red signal level, the values of which range from 0 to 255.

Although this technique is responsible for a theoretical maximum of 65536 brightness levels, in practice the number of control levels that can be attained is significantly less. At some time the change in the signal level of the combined brightness control signal will become smaller than the noise that is always present in the system.

The advantage of this technique is that when introduced, the controlling software can be configured to provide any number of brightness control levels, ranging from $2^8$ to $2^{16}$.

This is attained in that the most significant 8 bits of the necessary brightness value are arranged in the green color channel. The other bits of the necessary brightness value are arranged in the most significant bits of the red channel.

$$\text{Green} = \frac{(Brightness_{16} \wedge 1111111100\ 000000\ B)}{11111111B}$$

$$\text{Red} = (Brightness_{16} \wedge 0000000011111111B) x 11111111B$$

In another embodiment, an adaptive step threshold algorithm (ASTA) is used that is a threshold estimating algorithm that uses a few special techniques.

Each target position can be assigned to different strategies of steps.

A rapid sequence can be assigned to each position that passes through in excess of a single threshold value within the 95th percentile of the age-related normal values for the stimulus position. The start value for each psychophysical step threshold value estimating algorithm is set by its neighbor and develops from four initial set points that all pass through a complete step (4-2-2)-sequence. The start value for all of these secondary points is a pre-specified number of decibels below the adjacent threshold. A 2-2 step is used, but if the first threshold value excess seen is climbing and is within the 95th confidence interval, then the threshold value estimate has taken place.

Age-related normal data are formed in that non-linear methods are used for each stimulus site. Non-linear confidence limits are also established. This provides increased accuracy for the threshold estimation pattern and for data analysis.

The speed and accuracy of the algorithm can be changed by adapting the confidence interval permitted for a rapid sequence. For instance, the speed will increase and accuracy will decrease if larger confidence limits are used for the criterion of the rapid sequence.

There are two types of examination: i. First ASTA (iA-STA), which is used for establishing initial data. ii. ASTA that uses information from preceding fields (iA-STA or ASTA, an individual initial field, or the mean of a plurality of initial fields) in order to advance the step algorithm efficiently. iASTA uses a complete threshold value determination strategy. ASTA then uses the predetermined initial data to set the start values for each stimulus position and thus reduces the examination time.

Moreover, a hop limit strategy is preferably employed and/or used. Given the nature of the random point background, when the FDF stimulus is produced it is important to limit the change in contrast between successive representations. Limits that are especially based on empirical data are provided for each contrast step and a method for recording these maximum permissible steps is employed in the threshold value estimation algorithm (preferably ASTA). The limits are determined empirically and vary with respect to and/or as a function of eccentricity and defect depth. For instance, the limit for a stimulus contrast of 24 dB that is represented at an eccentricity of 3 degrees is or is pre-specified at 4 dB.

In another special embodiment, automatic control correction is used to compensate for deterioration, especially of the CRT phosphorus. The FDF instrument or the FDF unit requires that the brightness of the represented stimulus remains correctly adjusted. However, if a CRT is used, the luminosity of the phosphorus decreases with time for a specific control setting.

Similarly, the luminosity of an LCD unit or the brightness of a projection device or in general of the image generating unit can change with time.

The FDF unit includes a circuit that provides a means for measuring the brightness of the light generated by the image generating unit, such as CRT or LCD unit or projection device. The FDF unit periodically measures the brightness of the light generated by the image generating unit across its entire control range. This behavior is automatically corrected by monitoring the luminosity of the image generating unit and by controlling the control value using a microprocessor.

The circuit includes two photodiodes that scan the light from the image generating unit, such as the CRT or LCD or projection device. The signal from each photodiode controls a current to the voltage transformer, then an amplifier with programmable amplification. The programmable amplification is used to compensate individual sensitivities of the photodiodes. The prepared signal is then scanned with an ADC. At the time of production, a table is generated in order to provide a context between the ADC value and $cd/m^2$. The circuit essentially provides an instrument with a built-in light meter.

Obviously aging of the photodiodes themselves over time can cause changes in the displays of the photodiodes. To prevent this, two photodiodes are used as described in the foregoing. The measurement of luminosity is not accepted unless both photodiodes produce similar displays. Otherwise the user is informed that the apparatus requires testing or maintenance.

In one special embodiment of the invention, a method is provided for determining the correct position of the optic disc in the field of vision and its use. In order to be able to precisely determine the area of the field of vision that corresponds to a specific section of the optic disc and vice versa, it is important to know the precise relative position of the optic disc to the fovea. In one test, for instance with a retina tomograph, the patient focuses on a focusing target that has a fixed and known position relative to the optical axis of the instrument. All images obtained are arranged in the center about the optical axis of the instrument. In this way the center position of the optic disc within an obtained image permits the precise determination of the relative position of the optic disc to the fovea.

With this information it is possible
either to represent the stimulus at the correction positions during the field of vision examination such that a certain area of the field of vision corresponds precisely to a certain section of the optic disc;
or to plot the field of vision examination results after the field of vision examination such that certain areas of the field of vision are correctly assigned to certain sections of the optic disc.

In the inventive apparatus, in addition to the combination and/or integration of the FDF unit in the apparatus or the device with which the structures of the eye are examined and/or detected and/or evaluated, the method measures or functions explained in the foregoing are combined individually or a few at a time or all of them are combined and are realized by means of the computer, whether as hardware or software. The invention moreover includes the use of the inventively proposed and/or embodied apparatus.

Special embodiments and refinements of the invention, specifically of both the method and the apparatus, are depicted in the drawings and described in the following, but this shall not constitute any limit.

DETAILED DESCRIPTION OF THE INVENTION

Figure 1:
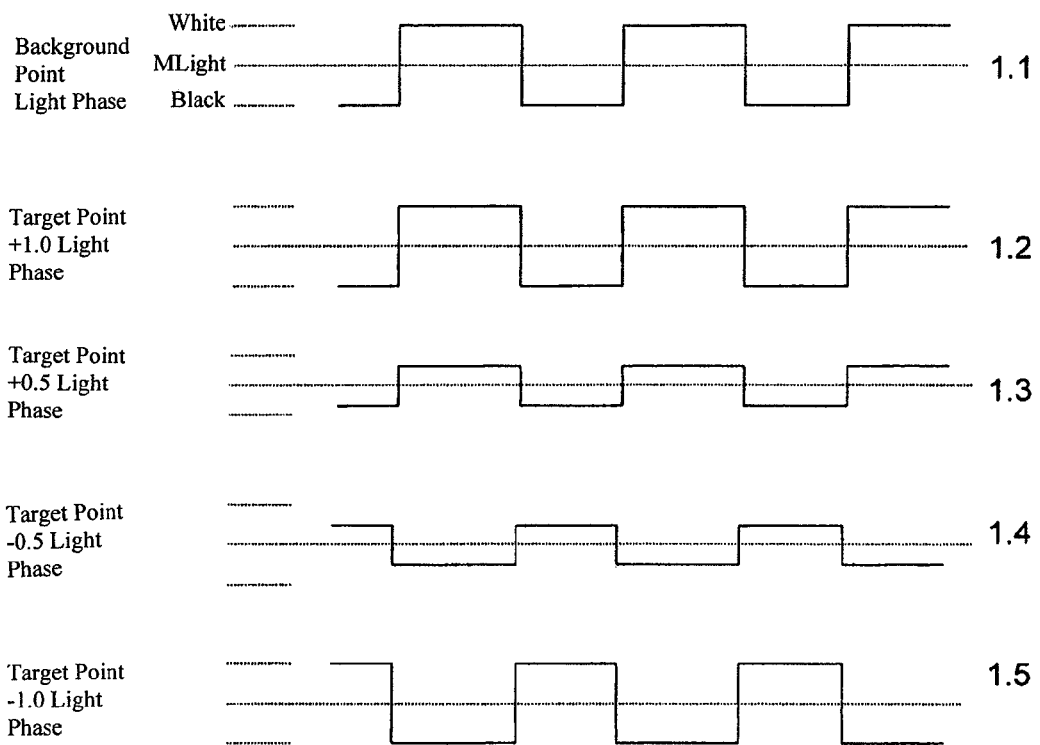
FIG. 1 provides diagrams of the background points and the target points of the image generating unit for determining an artifact.

Determining an artifact or the stimulus beginning for correcting or detecting an artifact shall be explained using FIG. 1. An FDF stimulus uses the image generating unit, on which a plurality of small circular objects or points are displayed on a solid background. The recordable and/or useable surface of the image generating unit is preferably at least almost completely filled with such points. These points are classified in two categories, specifically background points and target points. The background points preferably cover the majority of the visible display unit. A circular area in the display unit is provided for displaying the stimulus and those points that are disposed within the area of the stimulus are classified as target points. During the representation of the FDF stimulus, the points move back and forth between two brightness or intensity values at a pre-specified fixed frequency. The first step or a first level is an established brightness or luminosity value above the background brightness or background luminosity. The second brightness or intensity has the same value of luminosity or brightness below the background luminosity. It should be noted that the background points and the target points are in phase opposition when the stimulus is being represented. If e.g. the target points are brighter than the background luminosity, then the background points are darker than the background luminosity and vice versa. If the background points and the target points are now in phase, the display unit or image generating unit seems to flicker homogeneously. However, if the background points and target points are in opposing phases, a shadow-like ring appears around the perimeter and/or outer area of the target point area.

When an FDF stimulus is represented, the sudden change in the stimulus point from being in-phase with the background points to a 180° phase shift results in an artifact, the stimulus temporarily appearing brighter than the surrounding point field. The basis for the artifact is physiophysical in nature and is not based on abnormal or anormal brightness levels. The same artifact also occurs with a shift in stimulus.

The methods or the technique that is used to correct this artifact includes the gradual transition in the target point reversal from in-phase with the background points to phase-shifted. Starting with the reversal of the target points being in-phase with the background points, the amplitude of the target point reversal is reduced in a plurality of steps until the amplitude reaches zero. The amplitude of the target points then increases when the peak strength is in phase opposition to the background points.

The progression is depicted in the diagram in FIG. 1. The first wave 1.1 represents the cycle of the background points between values for the monochrome luminosity or between monochrome brightness values in a symmetrical manner about the mean luminosity or mean brightness. The next four waves 1.2 to 1.4 depict the progression of the brightness for the target points or target point luminosity from in-phase to 180° phase-shift relative to the luminosity or brightness of the background points.

Figure 2:
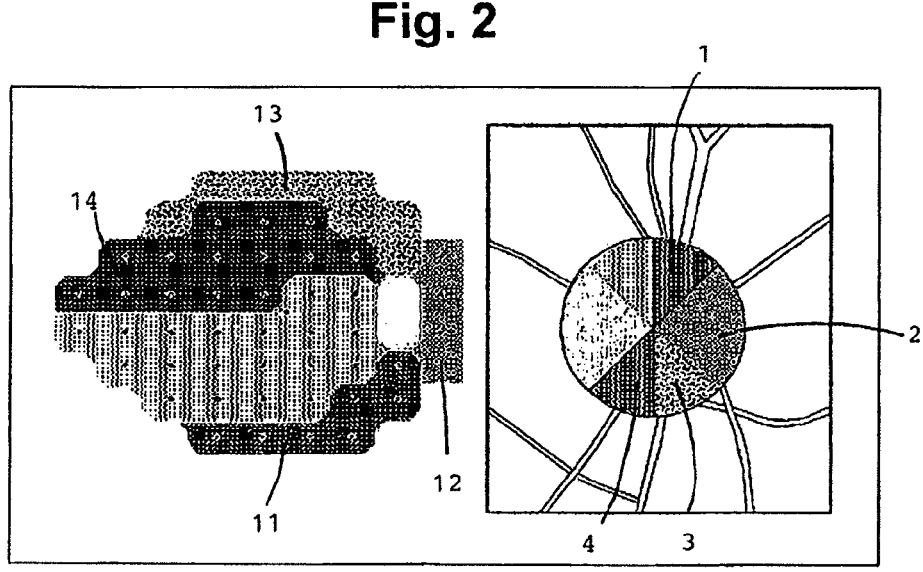
FIG. 2 depicts the optic disc and the field of vision.

FIG. 2 explains a special embodiment of the invention, specifically a structure-function analysis, in greater detail. A number of diseases of the posterior segment of the eyeball, for instance glaucoma, lead both to changes in the field of vision (functional changes) and to changes in the structure of the optic disc (structural changes). It is important to be able to evaluate the function and the structure in order to diagnose such diseases or to detect the progression of such diseases.

The inventive combination of the FDF unit, for instance an FDF perimeter, and a device or an apparatus with which structures of the eye, especially the optic disc structure, are examined and/or detected and/or evaluated, for instance a retina tomograph, makes possible a unique combined analysis of structure and function. This is based on the known assignment of certain segments, especially the optic disc, to certain areas of the field of vision.

The right-hand side of FIG. 2 depicts the optic disc divided into six different segments 1 through 6 and the left-hand side depicts the field of vision divided into six different areas 11 through 16. Segment 1 corresponds to the area 11, segment 2 corresponds to area 12, etc. The optic disc segments and the field of vision areas that correspond to one another have the same coding, especially color coding. Thus for instance segment 1 is coded red and so is area 11, and furthermore segment 2 is coded green, as is area 12, and the other segments and areas that are assigned to one another each have matching color coding. The segments of the optic disc and the areas of the field of vision assigned to them can also be coded with graphic patterns, as is depicted in black and white in FIG. 2. Furthermore, the number of segments and areas can be pre-specified according to the requirements.

Each segment of the optic disc and each area of the field of vision is divided into one of two or more categories. For instance, one set can have three categories: "within normal limits", "at the limit", and "outside normal limits". The methods explained in the following are used in order to represent these results to the person performing the examination, in particular the physician.

Figure 3:
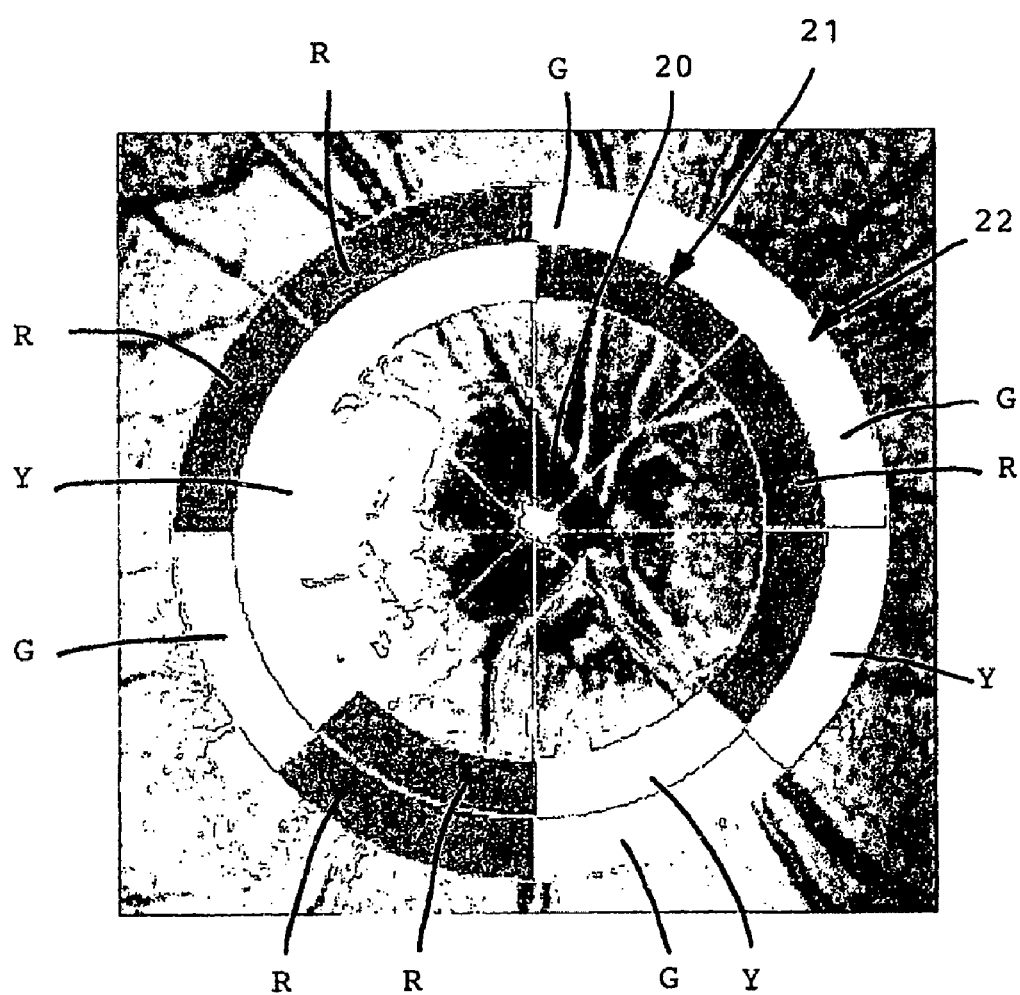
FIG. 3 depicts an image of the optic disc corresponding to the structural classification.

A first method is explained using FIG. 3, in which an image of the optic disc 20 is depicted and is divided into two or more segments; in this case it is divided into eight segments. Two rings 21, 22 that are divided into the same segments are superimposed. The inner ring 21 displays the results of the structural classification for every segment of the optic disc using a color code, for instance green G for "within normal limits", yellow Y for "at the limit", red R for "outside normal limits". The outer ring uses the same color code to display the classification results for the area of the field of vision that corresponds to a segment of the optic disc.

Figure 4:
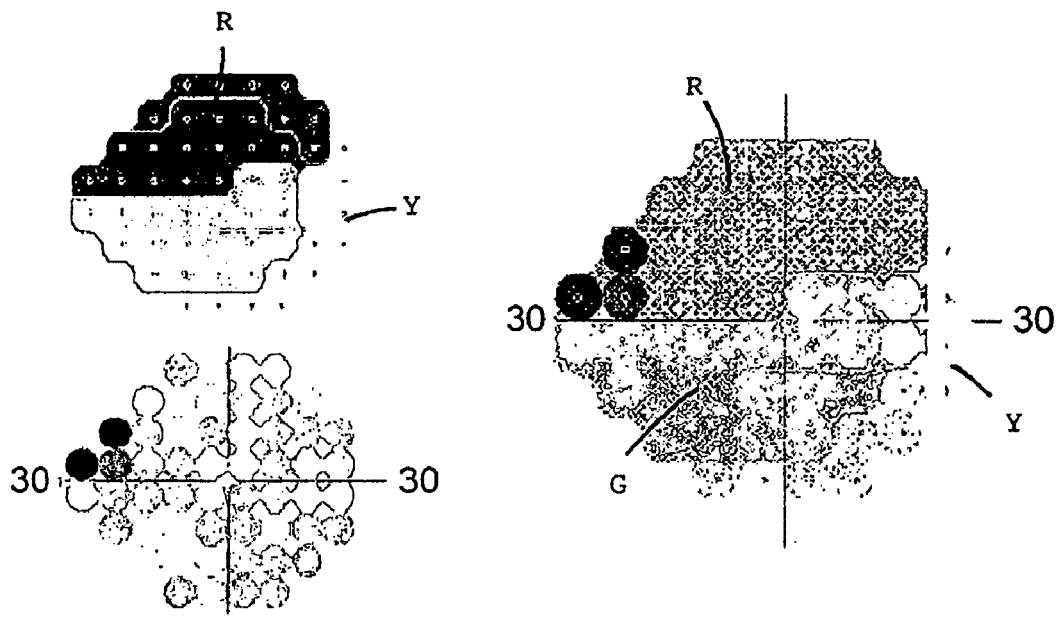
FIG. 4 provides representations of the field of vision results.

Explained in FIG. 4 is a second method, the field of vision results being depicted using the display of an image having the field of vision results for each stimulus position. The entire field of vision is divided into two or more areas that correspond to certain segments of the optic disc. The background for each field of vision area is color-coded, as explained in the foregoing, corresponding to the classification results for the optic disc structure that corresponds to this area.

In addition, in a third method the two measurements provided by the structural evaluation and the field of vision evaluation can be combined with respect to estimating normal, age-related ganglion cell density. This can be plotted by the clockwise positions of optic disc segments, in a manner similar to the known TSNIT plot, with the ganglion as the ordinate, and both measurements of structure and function plotted per segment on the abscissa.

Figure 5:
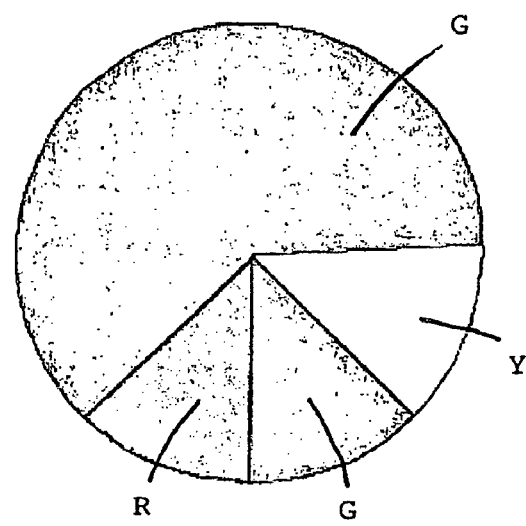
FIG. 5 is another representation of the field of vision results.

Finally, in a fourth method in accordance with FIG. 5, the field of vision results can be superimposed in an image of the optic disc such that each optic disc segment is color-coded in accordance with the field of vision results in its corresponding area of the field of vision.

The special features and refinements explained using the drawing are handled for the area of the optic disc. In the framework of the invention, these special features and refinements can be provided for other areas of the eye, such as the macula, or for other areas of the retina, analogous to those covered in the foregoing.

The invention claimed is:

1. Method for evaluating a field of vision, wherein flicked defined stimuli are represented using a plurality of points, which are classified into background points covering a majority of a display unit and target points located in a predetermined area of the display unit, wherein intensity values of the plurality of points move back and forth at a fixed frequency and the background points and target points are in phase opposition and are detected by a person having at least one eye to be examined, wherein a combination of results of a field of vision examination and results of a detection and evaluation of structures or structural changes in an eye area of the at least one eye provide that at least two areas of the field of vision are associated accordingly with segments of said eye area to be examined and depicted with matching coding, said eye areas of the field of vision and the accordingly associated segments of the eye area are divided into two or more categories (G, Y, R) in accordance with predetermined limits, and said combination of results are depicted in a representation of the field of vision result or an image of the examined eye area.

2. Method for evaluating a field of vision of at least one eye of a person by use of an optical instrument, comprising providing flicker defined from stimuli on a display unit for viewing by the person, the flicker defined form stimuli comprising background points covering a major portion of area of the display and target points in a circular area of the display, intensity of the points being alternated at a predetermined fixed frequency and the background points and target points being in phase opposition, wherein the flicker defined form stimuli are generated on the display unit by means of an image generating unit of a computer-controlled system, and wherein the displayed flicker defined form stimulus is subject to artifact correction, a target point reversal gradually transitioning from being in-phase to a phase-shift condition relative to the background points.

3. Method in accordance with claim 1, further comprising monitoring gaze of the person in real time for evaluating fatigue in the person, targets being provided at different locations relative to an optical axis of the instrument or the image generating unit for focusing the eye while field of vision evaluation is being performed, and thereby verifying correctness of focusing by the person in a predetermined time period.

4. Method in accordance with claim 1, comprising evaluating reliability of the person by using continuous reaction time monitoring, wherein a time from initiation of a target representation and actuation of a response button by the person is considered reaction time.

5. Method in accordance with claim 1, further comprising detecting structures and/or structural changes in the eye thereby to detect functional changes in the eye.

6. Method in accordance with claim 1, further comprising performing a boundary field examination comprising arranging light sources physically or optically in a boundary field.

7. Method in accordance with claim 1, further comprising performing a boundary field examination wherein the display unit is monochrome and the boundary field examination comprises controlling an increased brightness resolution, two color channels being used for providing a predetermined number of brightness levels for the monochrome display unit.

8. Method in accordance with claim 3, further comprising using an adaptive step threshold algorithm for assigning each target location.

9. Method for evaluating a field of vision of at least one eye of a person by use of an optical instrument, comprising providing flicker defined from stimuli on a display unit for viewing by the person, the flicker defined form stimuli comprising background points covering a major portion of area of the display and target points in a circular area of the display, intensity of the points being alternated at a predetermined fixed frequency and the background points and target points being in phase opposition, wherein the flicker defined form stimuli are generated on the display unit by means of an image generating unit of a computer-controlled system, and further comprising applying a hop limit, a change in contrast between successive displays of flicker defined form stimuli being limited with respect to the background points.

10. Method in accordance with claim 1, further comprising performing a structure-function analysis, structure of the eye being evaluated and predetermined segments of the structure being allocated to predetermined areas of the field of vision.

11. Apparatus for evaluating a field of vision of at least one eye of a person, comprising:
a computer, an image generating unit controllable thereby and a display unit operatively connected to the image generating unit, the computer system being programmed so as to cause the image generating unit to generate on the display flicker defined form stimuli comprising background points covering a major portion of area of the display and target points in a predetermined area of the display unit; and
wherein intensity values of the plurality of points move back and forth at a fixed frequency and the background points and target points are in phase opposition and are detected by said person having at least one eye to be examined, wherein a combination of results of a field of vision examination and results of a detection and evaluation of structures or structural changes in an eye area of the at least one eye provide that at least two areas of the field of vision are associated accordingly with segments of said eye area to be examined and depicted with matching coding, said eye areas of the field of vision and the accordingly associated segments of the eye area are divided into two or more categories (G, Y, R) in accordance with predetermined limits, and said combination of results are depicted in a representation of the field of vision result or an image of the examined eye area.

12. Apparatus according to claim 11, further comprising, for detecting structure of the eye, a light source and a scanning device operatively connected to the computer and to the image generating unit for data transfer.

\* \* \* \* \*